United States Patent
Ma et al.

(10) Patent No.: US 11,064,970 B2
(45) Date of Patent: Jul. 20, 2021

(54) METHOD AND APPARATUS FOR VISUALIZING A MEDICAL INSTRUMENT UNDER ULTRASOUND GUIDANCE

(71) Applicant: FUJIFILM SonoSite, Inc., Bothell, WA (US)

(72) Inventors: Qinglin Ma, Kirkland, WA (US); Kerem Karadayi, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 436 days.

(21) Appl. No.: 15/612,634

(22) Filed: Jun. 2, 2017

(65) Prior Publication Data

US 2018/0153503 A1 Jun. 7, 2018

Related U.S. Application Data

(60) Provisional application No. 62/430,298, filed on Dec. 5, 2016.

(51) Int. Cl.
*A61B 8/08* (2006.01)
*A61B 8/14* (2006.01)
(Continued)

(52) U.S. Cl.
CPC .......... *A61B 8/0841* (2013.01); *A61B 5/0095* (2013.01); *A61B 5/061* (2013.01);
(Continued)

(58) Field of Classification Search
CPC . A61B 2576/00; A61B 5/0084; A61B 5/0095; A61B 5/06; A61B 5/061;
(Continued)

(56) References Cited

U.S. PATENT DOCUMENTS

| | | |
|---|---|---|
| 5,722,852 A | 3/1998 | Miek |
| 8,232,891 B2 | 7/2012 | Wu |
| | (Continued) | |

FOREIGN PATENT DOCUMENTS

| | | |
|---|---|---|
| JP | 2010005194 A | 1/2010 |
| JP | 2012231979 A | 11/2012 |
| KR | 20150053630 A | 5/2015 |

OTHER PUBLICATIONS

International Searching Authority, International Search Report and Written Opinion, PCT Application PCT/US2017/064662, dated Mar. 22, 2018, 10 pages.

(Continued)

*Primary Examiner* — Joanne M Hoffman
*Assistant Examiner* — Alexei Bykhovski
(74) *Attorney, Agent, or Firm* — Womble Bond Dickinson (US) LLP (57) ABSTRACT

Systems and methods of facilitating the viewing of interventional instruments (e.g., needles, catheters, guidewires, vascular filters, biopsy probes) are disclosed herein. In one embodiment, a portable, handheld or cart-based ultrasound imaging machine is connected to an external laser light source that transmits laser light to a tip of an interventional instrument via one or more optical fibers. The laser light is absorbed at the distal tip of the instrument and generates a photoacoustic signal. The ultrasound imaging machine creates an image by combining data from the received photoacoustic signals with ultrasound echo data to show both tissue in a region of interest and the tip of the interventional instrument.

20 Claims, 10 Drawing Sheets

(51) Int. Cl.
  *A61B 5/00* (2006.01)
  *A61B 5/06* (2006.01)
  *A61B 8/00* (2006.01)
(52) U.S. Cl.
  CPC .......... *A61B 5/6848* (2013.01); *A61B 8/5207* (2013.01); *A61B 5/0084* (2013.01); *A61B 5/06* (2013.01); *A61B 8/14* (2013.01); *A61B 8/463* (2013.01); *A61B 8/469* (2013.01); *A61B 8/5261* (2013.01); *A61B 2576/00* (2013.01)
(58) Field of Classification Search
  CPC ....... A61B 5/6848; A61B 8/0841; A61B 8/14; A61B 8/463; A61B 8/469; A61B 8/5207; A61B 8/5261
  See application file for complete search history.

(56) References Cited

U.S. PATENT DOCUMENTS

| | | | |
|---|---|---|---|
| 2005/0187471 A1* | 8/2005 | Kanayama | A61B 5/0091 600/437 |
| 2009/0289200 A1* | 11/2009 | Ishii | A61B 1/00009 250/459.1 |
| 2011/0021924 A1 | 1/2011 | Sethurarnan et al. | |
| 2011/0319743 A1* | 12/2011 | Satoh | A61B 8/4416 600/407 |
| 2012/0310081 A1 | 12/2012 | Adler et al. | |
| 2013/0226002 A1 | 8/2013 | Miyachi | |
| 2014/0378796 A1* | 12/2014 | Chen | A61B 5/6848 600/328 |
| 2015/0297092 A1 | 10/2015 | Irisawa | |
| 2016/0061650 A1 | 3/2016 | Sato | |
| 2016/0113622 A1 | 4/2016 | Kim et al. | |
| 2016/0287278 A1 | 10/2016 | Stigall et al. | |
| 2016/0321325 A1* | 11/2016 | Wang | G06F 16/93 |
| 2017/0079622 A1* | 3/2017 | O'Donnell | A61B 5/0035 |
| 2017/0128038 A1* | 5/2017 | Tsushima | A61B 8/5207 |
| 2017/0219555 A1 | 8/2017 | Nazzaro | |
| 2018/0310831 A1* | 11/2018 | Cheng | A61B 5/6851 |
| 2019/0008393 A1* | 1/2019 | Irisawa | A61B 5/0095 |

OTHER PUBLICATIONS

PCT International Preliminary Report on Patentability for PCT/US2017/064662 dated Jun. 11, 2019, 6 pages.
PCT International Search Report for PCT/US2017/064666 dated Mar. 29, 2018, 3 pages.
PCT Written Opinion of the International Searching Authority for PCT/US2017/064666 dated Mar. 29, 2018.
PCT International Preliminary Report on Patentability for PCT/US2017/064666 dated Jun. 11, 2019, 7 pages.
Jameco Electronics (Electromechanical Switches: Choosing the Right Switch), 2010 (Year: 2010).
Ertle et al. (The Illuminated Laser Warning Sign, Photonics Spectra, Photonics Media Press. Dec. 2007) (Year: 2007).
Telenkov, et al. (Photoacoustic correlation signal-to-noise ratio enhancement by coherent averaging and optical waveform optimization, Rev. Sci. Instrum. 84, 104907, pp. 1-7 (2013) (Year: 2013).

* cited by examiner

METHOD AND APPARATUS FOR VISUALIZING A MEDICAL INSTRUMENT UNDER ULTRASOUND GUIDANCE

RELATED APPLICATION

The present application claims the benefit of, and priority to, U.S. Provisional Application No. 62/430,298 filed Dec. 5, 2016, which is herein incorporated by reference in its entirety.

TECHNICAL FIELD

The following disclosure is generally directed to systems for detecting one or more interventional instruments in a subject. In particular, one or more aspects of the disclosed technology are directed toward systems for producing a photoacoustic signal at an end portion of a needle and for producing an ultrasound image in which the end portion of the needle can be seen.

BACKGROUND

Many medical procedures require the accurate placement of an instrument in the body. For example, during a nerve block procedure, a physician and their assistant attempt to place a needle for delivering anesthetic near a particular nerve. Because the tip of the needle is in the body and can bend as it is being advanced and the exact location of the nerve is unknown, different techniques and tools are available to help the physician determine if the needle tip is in the correct location. For example, nerve stimulators can help confirm the location of a needle tip in the proximity of a nerve by applying a small amount of electricity to the patient's body to stimulate the nearby nerve. If the correct muscle associated with the targeted nerve responds to the electricity, the operator knows that he/she has reached the proximity of the target nerve to be blocked, and can then inject a drug.

Conventional ultrasound needle guidance technology can also be used to determine a needle and nerve location. One method, for example, involves enhancing and/or modifying ultrasound imaging parameters to emphasize the shaft of a needle that is in the same plane as the ultrasound image. Another method involves the use of an echogenic needle having laser-etched patterns on the needle shaft that enhance specular reflectivity when the needle is placed in the subject at a steep angle. Some predictive methods infer the location of a needle and its tip using magnetic and/or optical sensors attached to an ultrasound transducer and/or a needle. These predictive methods can be cumbersome, however, adding bulk and cost to an ultrasound transducer and typically require substantial training. Furthermore, since the location of the needle tip is inferred, a bent needle can lead to inaccuracies in the predicted needle tip location.

Another approach that is being developed is to use photoacoustics to locate a needle tip. With this method, one or more laser light pulses are transmitted to an optical absorber at the distal tip of a needle that cause the absorber rapidly heat and expand on a microscopic scale compared to the surrounding tissue. The expansion creates ultrasonic vibrations that can be detected with an ultrasound transducer. While some ultrasound machines are being designed with the capability to interface with a laser source that delivers such laser pulses and detect the corresponding echo signals, there is a need to be able to use such techniques with older or less sophisticated ultrasound machines, or with machines that are not specifically designed to support a photoacoustic imaging mode. The disclosed technology simplifies the complexity and reduces the requirement for large a memory and a powerful processor that are typically required in conventional photoacoustic imaging.

DETAILED DESCRIPTION

The disclosed technology relates to systems and methods of facilitating interventional procedures such as, for example, the administration of anesthesia, MSK/sports medicine for joint/tendon/muscle injection, fine needle aspiration, amniocentesis, thoracentesis, pericardiocentesis, vascular access and biopsy. In one embodiment, a system includes an ultrasound imaging machine and an external laser light source that communicates with the ultrasound imaging machine to deliver light pulses to a tip of an interventional instrument (e.g., a needle, a catheter, a biopsy instrument, guidewire, vascular filter or the like). The ultrasound imaging machine is configured to transmit ultrasound energy into a region of interest of a subject (e.g., a human or an animal) and receive corresponding ultrasound echoes from the subject and the instrument. The laser light source generates one or more laser light pulses that are transmitted to a tip or a distal portion of the interventional instrument via one or more optical fibers. The distal end of the fiber is covered with a light absorbing material such as a black epoxy. The external laser light pulses are absorbed by such material in an area adjacent the distal tip of the interventional instrument, which causes photoacoustic signals to be produced.

In one embodiment, the light absorbing material is positioned at the tip of the fibers to absorb the laser light pulses and emit corresponding photoacoustic signals that the ultrasound imaging machine can detect. The ultrasound imaging machine receives the photoacoustic signals and produces real-time line data for use in creating an ultrasound image of the tip of the interventional instrument based on the detected photoacoustic signals. In some embodiments, the ultrasound imaging machine is configured to produce an ultrasound image of the interventional instrument using a color map. The machine can process the signals to form a colorized ultrasound image that is superimposed on or combined with, a normal gray-scale tissue image. As a result, the user can visualize a colored set of pixels in a combined ultrasound image to show the instrument tip in real time. The machine can be configured to receive a user command to turn this feature on/off and control the intensity or brightness of the colored image via gain or laser output power manipulation within the allowed regulatory requirements. The machine can also be configured to receive user input regarding a desired color for the displayed image of the instrument tip. In some embodiments, a signal to automatically turn on the imaging mode is sent from the external laser light source when an interventional instrument is connected to reduce or simplify the user interaction. These and other embodiments of the disclosed technology are expected to provide more natural hand-eye coordination, more precise placement of the interventional instrument tip, reduced procedure times and/or enhanced instrument tip visualization compared to conventional instrument visualization techniques. This is especially helpful for steep angle insertions where it has been difficult to image a needle using traditional ultrasound imaging techniques. For out-of-plane insertions, the disclosed technology can tell the user if a needle tip has reached the imaging plane.

Figure 1A:
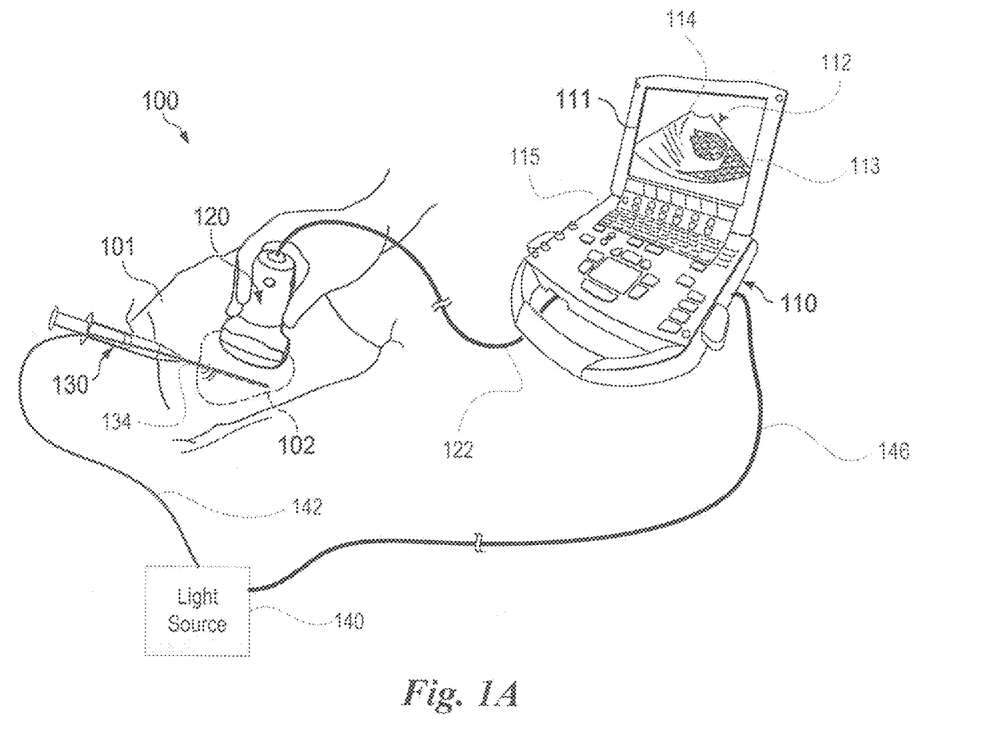
FIG. 1A illustrates an interventional instrument imaging system configured in accordance with an embodiment of the disclosed technology.
Figure 1B:
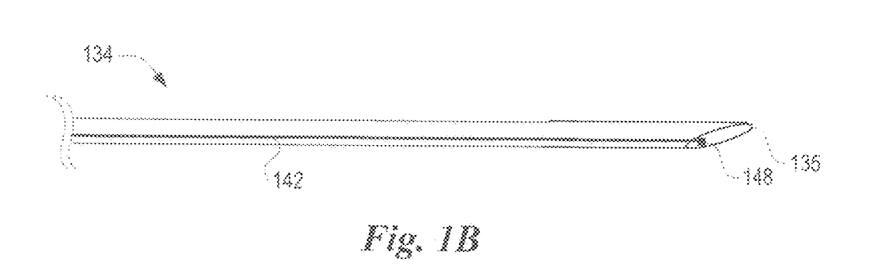
FIG. 1B illustrates one embodiment of a needle for use with the interventional instrument imaging system shown in FIG. 1A.

FIG. 1A is a partially schematic view of an interventional instrument imaging system 100 including an ultrasound imaging machine 110 coupled to an ultrasound transducer 120, an external laser light source 140 and an interventional instrument 130 (e.g., a needle). FIG. 1B is a schematic view of a shaft portion 134 of the interventional instrument 130. Referring to FIGS. 1A and 1B, the ultrasound transducer 120 is configured to transmit ultrasound energy into a region of interest 102 of a subject 101 and receive corresponding ultrasound echoes from the region of interest 102. A cable 122 carries electronic signals produced in response to the received ultrasound echoes from the transducer 120 to the ultrasound imaging machine 110. The ultrasound imaging machine 110 processes the electronic signals and generates one or more ultrasound images 113 that are displayed on a user interface 112 of a display 111. An input interface 115 receives user input and instructions via one or more user input controls (e.g., one or more buttons, keys, knobs, switches, sliders, trackballs and/or touch-sensitive surfaces).

Figure 1C:
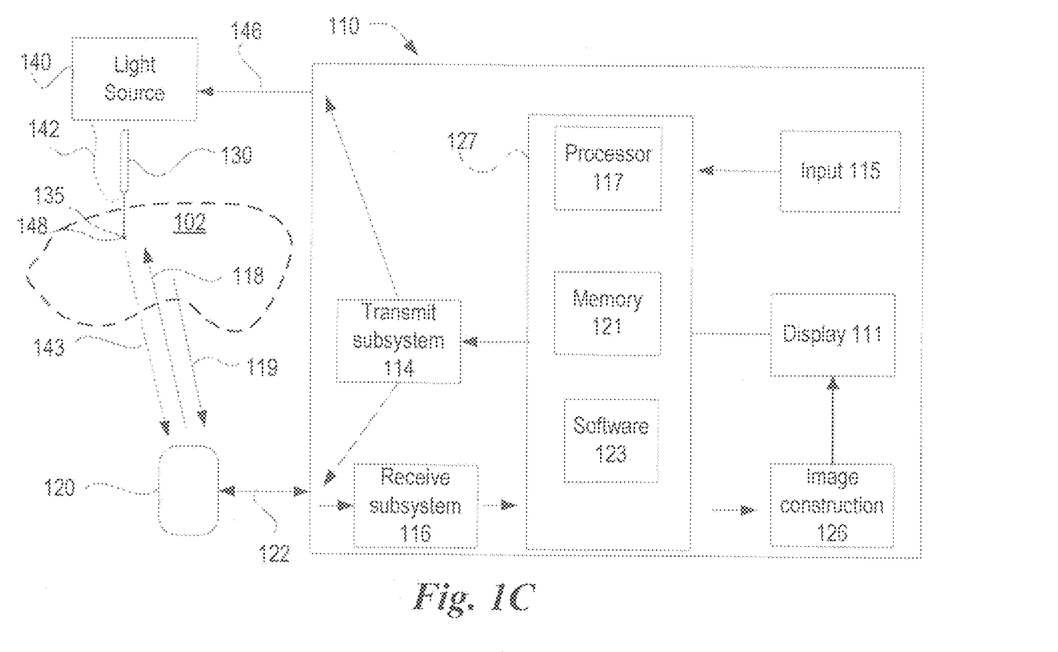
FIG. 1C is a functional block diagram of an ultrasound imaging machine of FIG. 1A during a photoacoustic imaging procedure in accordance with an embodiment of the disclosed technology.

Referring to FIGS. 1A-1C together, the external laser light source 140 (including a laser diode, miniaturized YAG, Alexandrite or other type of laser light source) communicates with a port such as an EKG port of the ultrasound imaging machine 110 via a connection cable 146 (e.g., a USB cable, I2C cable, ECG cable, an HDMI cable or a custom designed cable). In some embodiments, however, a wireless connection (e.g., Bluetooth, 802.11 etc.) can be used for communication between the laser light source 140 and the ultrasound machine 110. One or more optical fibers 142 extend from the laser light source 140 to a tip 135 (FIGS. 1B and 1C) of the shaft 134. In some embodiments, the one or more optical fibers 142 extend through an interior portion of the shaft 134. In other embodiments, however, the one or more optical fibers extend on an exterior surface of the shaft 134. Yet in another embodiment two or more channels of the needle could be used to house the fiber specifically. The one or more optical fibers 142 can be attached to the interior or the exterior surface of the shaft 134 with an epoxy or another adhesive to allow room for fluid flow inside the shaft of the interventional instrument 130. In some embodiments, a double or multi-lumen instrument separates the one or more optical fibers 142 from a fluid channel. In some embodiments, the exterior of the shaft 134 is free of markers, while in other embodiments, an outer surface of the shaft includes one or more markers that are used to indicate the depth to which shaft is inserted into a body.

Figure 3:
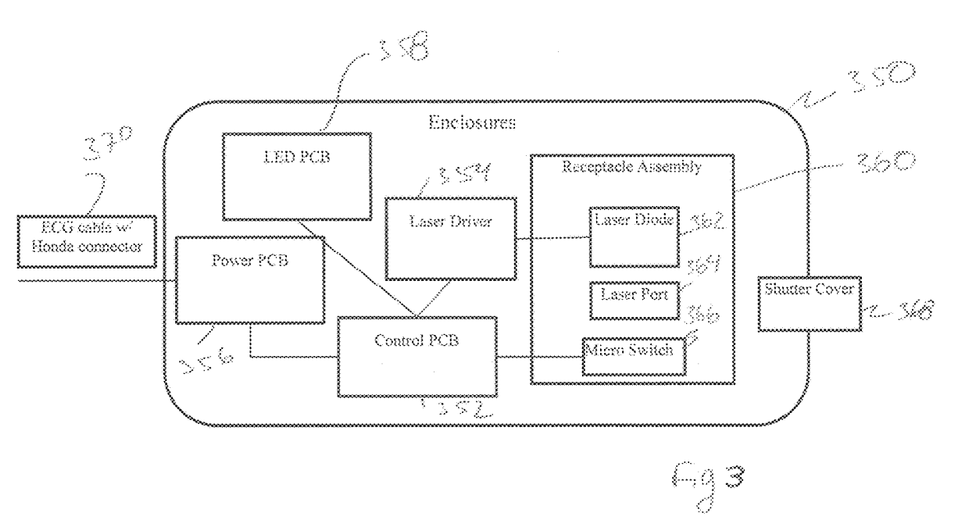
FIG. 3 is a functional block diagram of an external laser light source in accordance with an embodiment of the disclosed technology.

As will be explained in further detail below, the external laser light source 140 includes a system interface for power and communication, a memory for storing a device ID and program instructions, an optical assembly including a mechanical connector for engaging a fiber optic connector, a light shutter, a light ring and one or more LEDs that illuminate when the laser is activated.

The laser light source 140 is configured to produce one or more fixed or variable wavelength laser light pulses in the range of visible or invisible IR light (300 nm to 1500 nm) as an example, that are transmitted to the tip 135 via the one or more optical fibers 142. The duration of the laser pulses is selected so that the photoacoustic signals created at the tip of the instrument are in the receive bandwidth of the ultrasound transducer 120.

In some embodiments, a light absorbing medium 148 (FIG. 1B) is positioned at the tip 135 and covers the ends of the one or more fibers. The absorbing medium absorbs the one or more laser light pulses transmitted from the laser light source 140 and generates photoacoustic signals 143 (FIG. 1C). As shown in FIG. 1C, the ultrasound transducer 120 transmits ultrasound pulses 118 into a region of interest and detects ultrasound echoes 119 as well as the photoacoustic signals 143 that are created in response to the laser pulses. As explained in further detail below, the ultrasound imaging machine 110 forms one or more ultrasound images of tissue and the interventional instrument 130 in the region of interest 102 using the detected ultrasound echoes 119 and the photoacoustic signals 143. As those of ordinary skill in the art will appreciate, because the photoacoustic signals 143 originate only from the needle tip, the source of the photoacoustic signals 143 is the tip location. In one embodiment, the ultrasound imaging machine 110 creates data for two images (e.g. from the returned ultrasound echoes and the received photoacoustic signals respectively), and combines the data for both images to create a combined image in which the colored tip of the instrument is shown to the user among the normal gray scale tissue image. In some embodiments, the pixels representing the tip of the instrument are colorized differently from a traditional gray scale ultrasound tissue image to increase the contrast or awareness of the tip location. Note the photoacoustic image is an ultrasound real time image created in response to photoacoustic signals that originate directly from the location of the needle tip, not a graphical indicator that is derived from some other inputs. Therefore, it is not prone to the bending of the needle shaft and is applicable for any angle of insertion including out-of-plane methods.

In some embodiments, the light absorbing medium 148 at the distal end of the instrument is an epoxy that absorbs the laser light pulses and emits corresponding photoacoustic signals 143 (FIG. 1C). As those of ordinary skill in the art will appreciate, the absorption of the individual laser light pulses increases the temperature of the light absorbing medium 148. The resulting temperature increase causes the light absorbing medium 148 to expand and produce the photoacoustic signals 143 that can be detected by the transducer 120. Because the photoacoustic signals 143 are only emitted from the tip 135, the ultrasound imaging machine can produce an image of the tip 135 directly without using another method to infer the location of the shaft 134 and/or the tip 135.

In some embodiments, the light absorbing medium 148 may comprise, for example, an epoxy, a polymer, a plastic and/or another suitable material that can stick to the fiber(s) and absorb the laser light to generate the photoacoustic signals. One benefit of using a light absorbing material is prevention and/or reduction of light leakage into the tissue that itself could generate photoacoustic signals, which could cause ambiguity of the needle tip location. In other embodiments, the ends of the one or more optical fibers are silvered or otherwise coated with a metal or other material that absorbs the laser pulses. In still other embodiments, the optical fibers are angled, cut or lensed so that the laser light pulses are directed onto the distal end of the interventional instrument or into the tissue. The material that absorbs the pulses then generates the photoacoustic signals in a manner that is similar to that of the black epoxy.

Line-Based Imaging

Figure 1D:
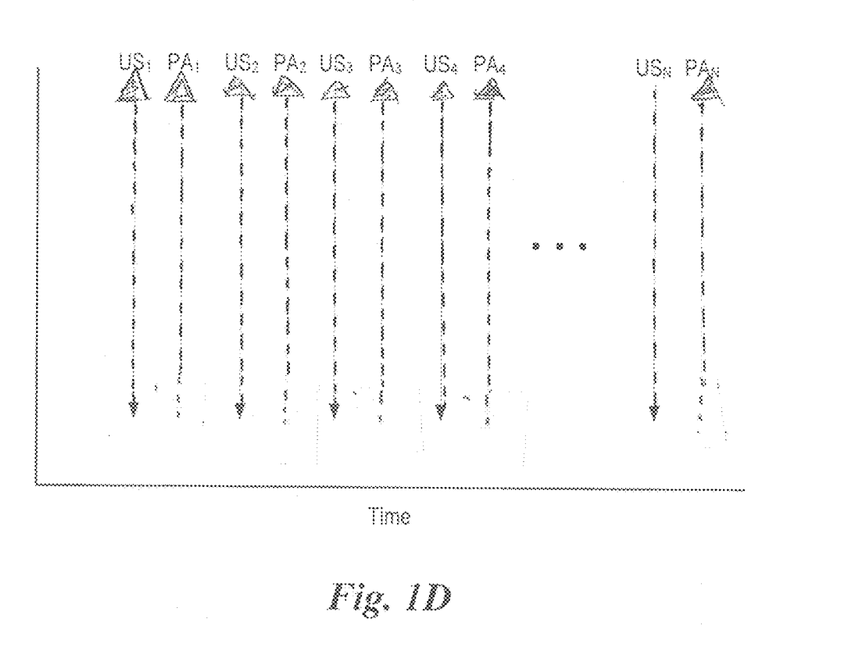
FIG. 1D is a timing diagram showing an example of a transmission and receiving sequence of interleaved ultrasound and photoacoustic line signals in accordance with an embodiment of the disclosed technology.

In the illustrated embodiment of FIGS. 1C and 1D, the ultrasound imaging machine 110 (e.g., a portable ultrasound machine) is configured to support line triggered laser firings and to use conventional beamforming paths to form photoacoustic image lines that are interleaved with lines created for B-mode imaging. In one embodiment, the ultrasound imaging machine 110 is configured to interleave the ultrasound and laser pulse firings. The machine transmits the ultrasound pulses 118 and receives the corresponding ultrasound echoes 119 to form a line of a B-mode ultrasound image frame. It then switches to the photoacoustic imaging mode by halting or suspending the ultrasound machine's transmission electronics or by causing the transmit electronics to produce ultrasound signals with little or no energy and sending one or more trigger signals to the external laser light source 140 to cause the production of one or more of the laser pulses. Photoacoustic signals are then created in response to the one or more laser pulse firings.

Figure 1E:
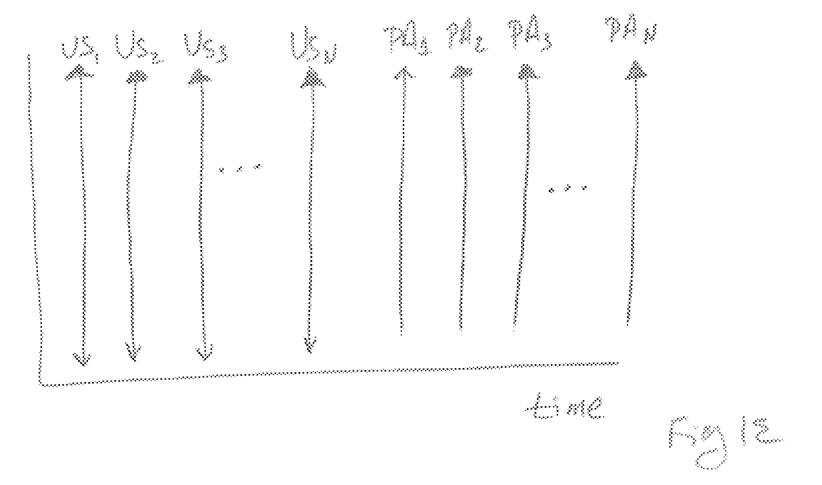
FIG. 1E is a timing diagram of a transmit and receive sequence for ultrasound lines received for a B-mode imaging frame followed by a number of photoacoustic lines received for a photoacoustic imaging frame in accordance with an embodiment of the disclosed technology.
Figure 1F:
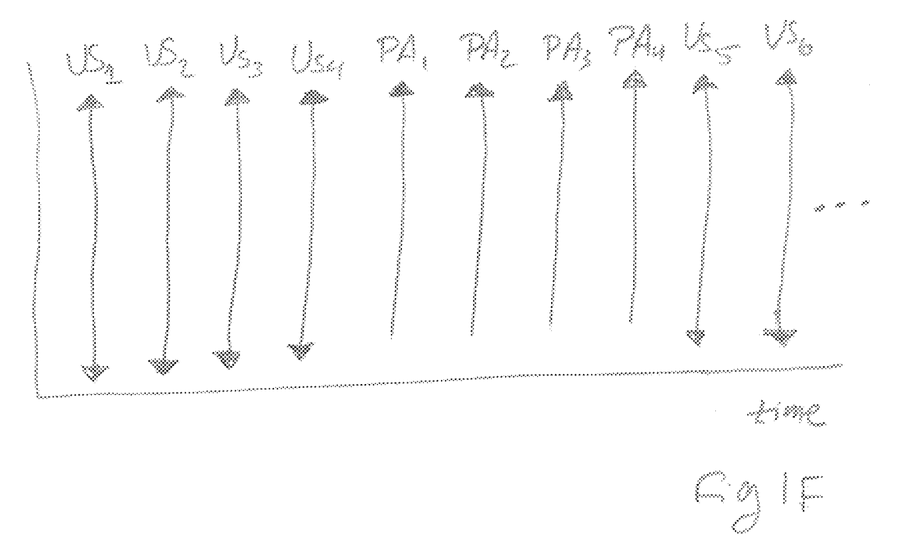
FIG. 1F shows interleaved blocks of ultrasound lines received for a B-mode imaging frame and blocks of photoacoustic lines received for a photoacoustic imaging frame in accordance with an embodiment of the disclosed technology.

In the embodiment shown in FIG. 1D, ultrasound lines (US) for a B-mode image frame are alternately produced with photoacoustic lines (PA) for a photoacoustic image frame. Alternately, as shown in FIG. 1E, an entire set of N ultrasound signals (US1-USN) can be created for a B-mode image frame followed by a set of laser firings to produce a set of photoacoustic lines (PA1-PAN). Alternating blocks of ultrasound signals and laser firings can also be obtained as shown in FIG. 1F. In some embodiments, one or more laser pulses are transmitted for each line used in making a photoacoustic imaging frame.

Figure 2A:
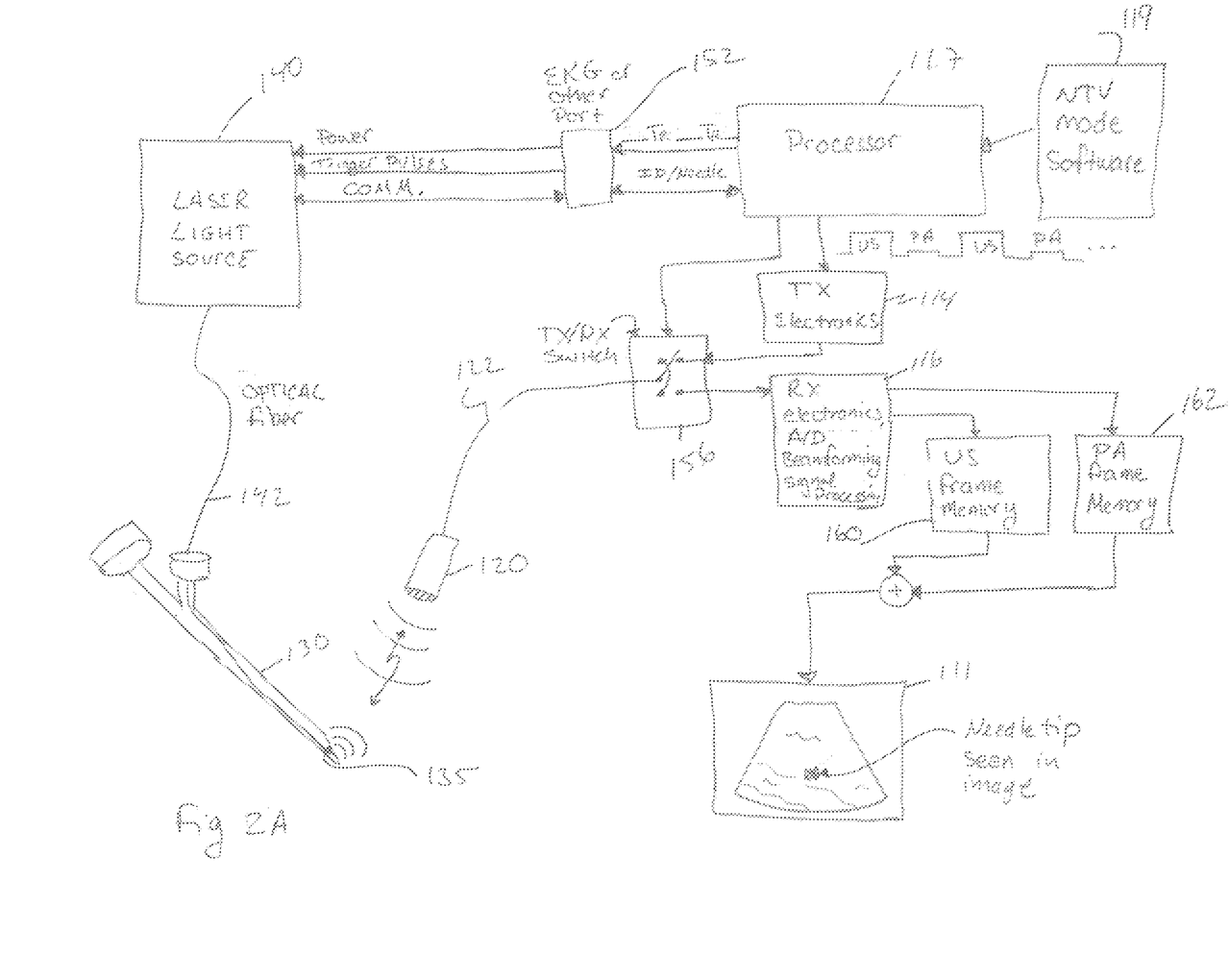
FIG. 2A is a functional block diagram of an ultrasound imaging machine designed to produce an image of a tip of an interventional instrument using photoacoustic signals in accordance with some embodiments of the disclosed technology.

FIG. 2A illustrates further detail of one embodiment an ultrasound imaging machine that is programmed to produce images of a needle tip using the photoacoustic signals. The ultrasound system includes one or more processors 117 that are programmed to execute needle tip visualization (NTV) software when an operator wants to visualize the position of a needle using photoacoustics. After connecting the external laser light source 140 to a port (EKG, USB or other port) 152 on the ultrasound machine, the laser light source 140 communicates a device ID to the processor 117 to inform the machine that the laser light source 140 is connected. In one embodiment, power for the external laser light source 140 is provided from the ultrasound machine to the laser light source 140 through the port 152. However, the laser light source 140 could be powered by a battery or from another power source (external power supply) if desired.

Conventional photoacoustic imaging is done mostly by obtaining radio frequency element data and using the data to form a photoacoustic image. The beamforming is done not using an existing delay-and-sum hardware based beamformer but a fast CPU or GPU are programmed to do software-based beamforming. Since this approach is slow compared to a hardware-based approach, a fast beamforming method called FFT beamforming is used. However, it only applies to a linear transducer. To accommodate both normal imaging and photoacoustic imaging, either the normal imaging has to be moved to the FFT-based software beamformer or additional processing power has to be provided to support both methods. In some embodiments described, this obstacle is alleviated by not requiring a software-based beamformer but instead utilizing an existing hardware-based beamformer for photoacoustic imaging.

As indicated above, some ultrasound imaging machines do not have specialized hardware support for photoacoustic imaging (also referred as needle tip visualization mode—NTV). For these ultrasound machines, the operating software is modified so that the machine can produce data for two images that are blended together where the data for one of the images is created from the received photoacoustic signals. In accordance with one embodiment of the disclosed technology, when operating in the NTV mode, the processor 117 executes NTV software instructions 119 that cause the processor 117 (or the transmit electronics 114) to generate a trigger signal (labelled Tr) when the laser light source 140 is to produce a laser light pulse. In some embodiments, the processor 117 also instructs the transmit electronics 114 to reduce the amplitude or the duration of a transmit pulse at the time when the laser light pulse is produced by the external laser light source so that little or no ultrasound energy is produced by the ultrasound transducer 120. Upon receipt of the trigger pulse, the laser light source starts the sequence of producing one or more laser pulses, which cause photoacoustic signals to be generated near the needle tip. Receive electronics 116 in the ultrasound system 110 are then enabled to detect the photoacoustic signals.

A transmit/receive switch 156 is used to protect the sensitive receive electronics 116 from the large voltages produced by the transmit electronics 114 and other transients. After one or more pulses have been transmitted by the ultrasound transducer 120 for the acquisition of a line for a B-mode imaging frame, the position of the transmit/receive switch 156 is changed by the processor 117 so that the receive electronics 116 begin detecting the return echo signals from a desired distance away from the transducer (e.g. the skin line). During a photoacoustic line acquisition, the receive electronics are controlled to begin receiving signals from the same positions away from the transducer as the lines in the ultrasound frame for correct spatial registration of the PA frame with the normal B-mode frame. In some embodiments, the position of the transmit/receive switch 156 can remain closed after a B-mode line is received. Keeping the switch closed avoids electrical noise associated with opening and closing the switch 156 that causes artifacts.

Echo signals created in response to the B-mode firings are two-way beamformed and signal processed and may be stored in a B-mode image frame memory 160 until all the line data required to produce a frame are obtained. Similarly, one-way beamformed and signal processed photoacoustic signals may be stored in a second image frame memory 162 (labelled photoacoustic PA memory). Once all the line data for both frames are obtained, the processor 117 combines data from each frame to produce a composite image in which the tissue in the region of interest and the position of the tip of the instrument can be seen.

As indicated above, because the ultrasound imaging system 110 is not specially designed to perform photoacoustic imaging, the system uses the existing receive electronics 116 to process the photoacoustic signals. In one embodiment, the system is programmed to operate as if it transmits ultrasound from the imaging transducer but the transmit electronics are controlled to transmit pulses with minimal or no energy by reducing the amplitude of the pulses to zero or by setting their pulse length to zero. Minimal energy can be zero energy or an energy level that is small enough such that the pulses do not interfere with the ability of the ultrasound imaging machine to accurately detect the photoacoustic signals.

In some embodiments, the ultrasound imaging machine behaves as if it transmitting ultrasound into the body and detecting the corresponding echo signals when in fact the received echo signals are being generated in response to the one or more laser pulses. The laser pulse firings are synchronized with the transmission of the minimal energy ultrasound beams. In other embodiments, the transmit electronics of the ultrasound imaging machine are disabled or suspended at times when the laser pulses are transmitted.

In some embodiments, the processor 117 is programmed to operate the transmit electronics 114 in a mode where photoacoustic lines are alternatively received with B-mode lines but no ultrasound pulses are transmitted. Many ultrasound imaging machines have the ability to alternate firings for B-mode images with another imaging mode. For example, many ultrasound machines can operate in Color Power Doppler (CPD) mode where lines to produce a CPD image frame are interleaved with B-modes lines. However, because the photoacoustic signals are received without a transmission from the ultrasound transducer, the processor changes the transmit amplitude and/or the duration of the transmit pulses for the PA lines to zero so that minimal or no ultrasound energy is delivered by the ultrasound transducer 120 at the time when the laser pulse are being delivered. In addition, the processor is programmed to produce a trigger signal each time the system fires these zero energy pulses. The trigger pulses are transmitted via a wired or wireless communication link to the external laser light source 140 where the pulses are used to trigger the production of corresponding laser pulses.

The receive electronics 116 are instructed to function once a light pulse is fired by the laser source through a T/R switch or other means. In some embodiments, for example, the T/R switch 156 is open during transmit to protect the receive electronics 116 from high voltages or other electrical anomalies. Once the transmit pulse is fired, the receive electronics 116 begin to process the echo signals received by the imaging transducer 120. A system timer starts to store the received signals at a time that equates to a desired distance in the region of interest assuming a constant sound speed in tissue of 1540 m/s. In one embodiment, time zero is equated with echo signals at the skin line and at a maximum time, echo signals are equated to the deepest depth in the region of interest (e.g. in a range of 1 to 30 cm).

For photoacoustic imaging, the processor 117 sends or causes other electronics to send, a trigger signal to the laser light source 140 each time an ultrasound pulse is produced (though the transmitter is programmed to transmit pulses with minimal or zero energy) for each or multi-receive lines and each time a laser pulse is requested. The laser light source 140 fires the laser once the trigger signal is received. As shown in FIG. 2C, an appropriate trigger delay $\Delta t$ is used to compensate for a delay between the time when the trigger signal is transmitted to the external laser light source 140 and the time at which the laser pulse is actually fired. This delay could be determined based on a theoretical analysis value or an empirical value selected to align the photoacoustic image frame with the normal background gray-scale tissue image frame.

The received echo signals for each imaging frame go through beamforming, signal and image processing chains for each line to form an image frame. Multiple receive lines can be formed by each laser firing depending on the system architecture. Most conventional ultrasound imaging machines can form 1-4 receive lines from each transmit beam. In one embodiment, a receive line is created for each laser firing. In this mode, the laser is fired multiple times (e.g. ranging from 32 to 256 times) to create a frame of photoacoustic imaging data.

The modifications for the NTV mode include at least a receive delay calculation based on one-way propagation instead of two-way propagation, received sample registration of wave propagation times, scan conversion modifications if a different number of lines are used for the photoacoustic frame from the normal B-mode frame, color map for photoacoustic image, photoacoustic/tissue decision, blending/combination, CINE for PA+B-mode, clip storage, etc.

Care must be taken to align the PA axial samples in space since it is a one-way data. If the same RF sampling frequency is used (most machines use 40 MHz or so) for photoacoustic data as B-mode data, the spacing of the photoacoustic axial samples is twice the distance between the samples as that of the B-mode samples. Either upsampling or half the decimation rate can be used to have the same number of RF samples of the PA frame as that of the B-mode frame. The number of lines per frame could be the same or different for the photoacoustic mode. The more lines the better the shape of the tip image but the frame rate slows.

Figure 2B:
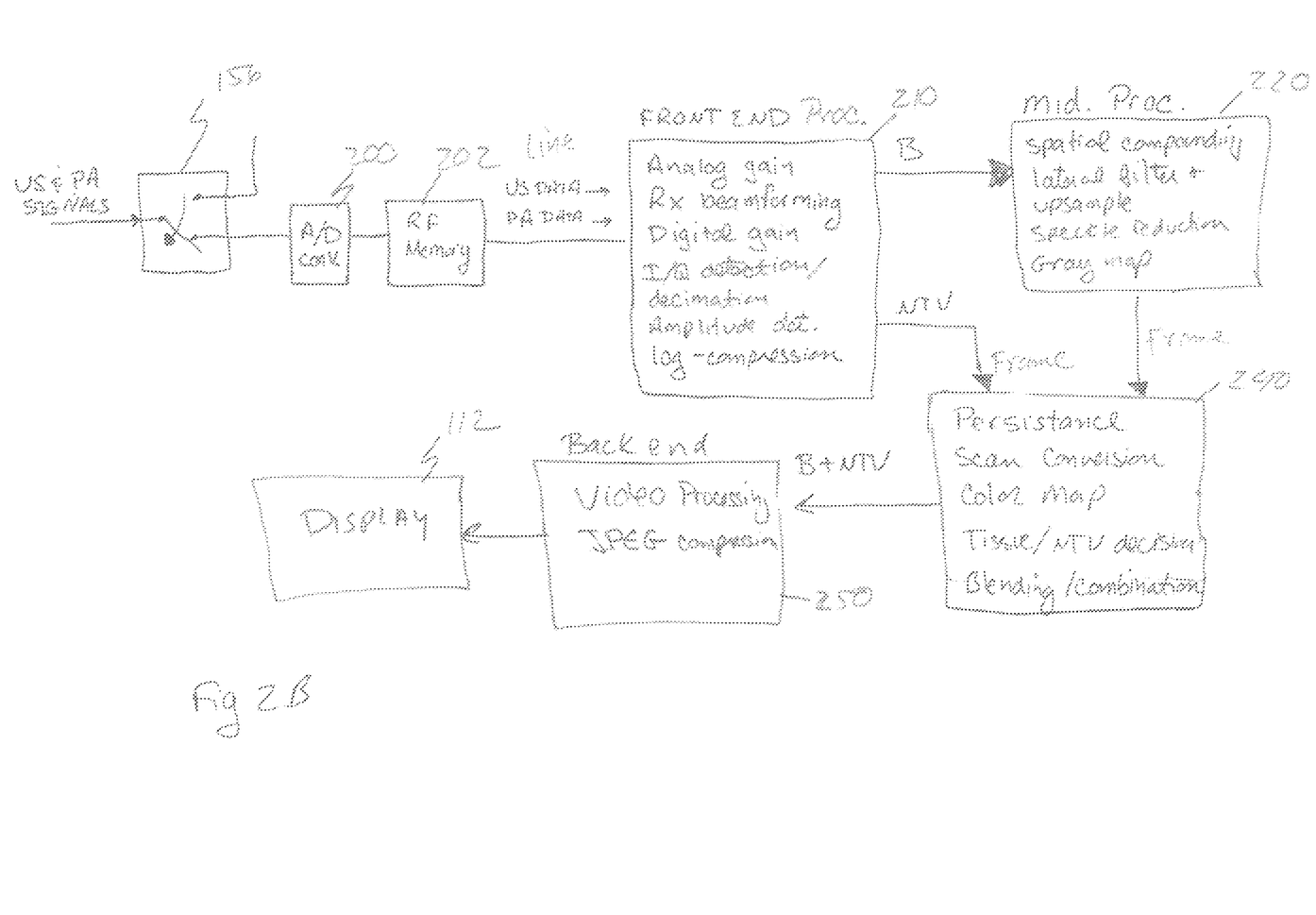
FIG. 2B shows a signal processing path in an ultrasound imaging machine to produce an image of tissue and a photoacoustic image of an interventional instrument in accordance with some embodiments of the disclosed technology.
Figure 2C:
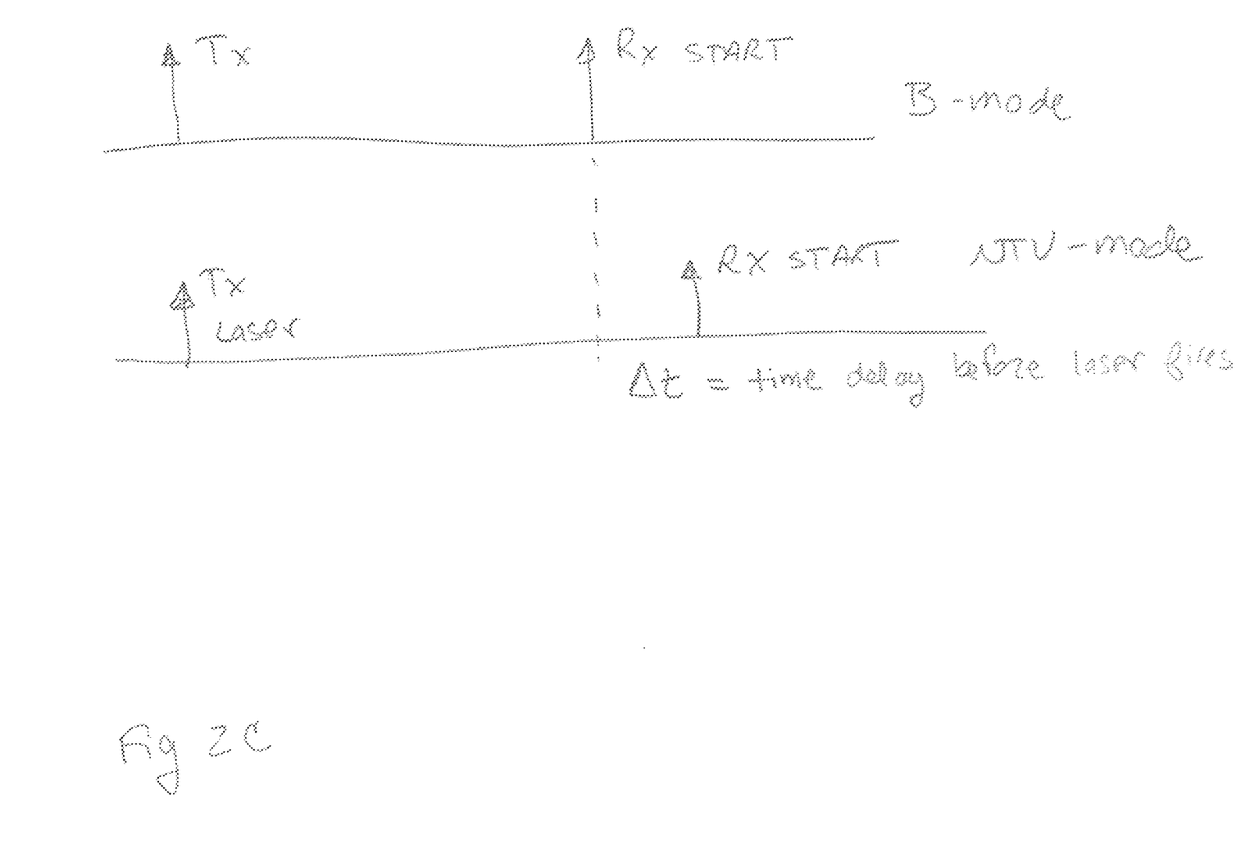
FIG. 2C shows how the timing of received photoacoustic signals in an ultrasound imaging machine can be adjusted to compensate for a delay in a laser firing in accordance with some embodiments of the disclosed technology.

FIG. 2B shows two different image processing paths used to process the B-mode line data and the photoacoustic line data (also referred to as NTV data) in accordance with an embodiment of the disclosed technology. Ultrasound and photoacoustic echo data are received through the transmit/receive switch 156 and converted to a digital format by an analog to digital converter 200. Digitized ultrasound and photoacoustic echo data may or may not be stored in an RF ultrasound memory 202 (in conventional ultrasound, they are not stored). The stored or real time data are then processed in slightly different imaging paths. Both the B-mode and the photoacoustic data are processed in a front-end image processor 210 (e.g. DSP, GPU or the like) that performs receive beamforming, adjusts the gain with a digital gain function, performs I/Q detection, amplitude detection and decimation. Note the receive delay applied to the photoacoustic samples is different from that of the B-mode. It is calculated or pre-stored table for one-way propagation instead of two-way.

The B-mode echo data is then subjected to additional processing in a mid-processor 220 where the data are processed by spatial compounding, lateral filtering and up-sampling. Speckle reduction is also performed and a gray-scale map is applied to the B-mode line data. In one embodiment, the processed echo data and the photoacoustic/NTV line data are stored in a memory until the frames are completed.

Once the data is complete for a B-mode image frame and a photoacoustic/NTV image frame, the line data for both image frames are processed in a processor 240 by applying a persistence algorithm (it could be different algorithm or setting for each mode) and scan conversion to produce pixel data for a B-mode image and a photoacoustic/NTV image. Data for the NTV and B-mode image pixels are subjected to a different color map, where the needle tip pixels are displayed in a system or user selected color. Data for each image are then analyzed on a pixel by pixel basis to make a tissue/NTV decision that determines if the pixel data for the B-mode image or the NTV image should be displayed in a particular pixel location of a combined image. The tissue/NTV decision is very similar to the tissue/flow decision that could be a simple threshold-based algorithm or some more sophisticated algorithm based on multiple parameters. More sophisticated blending also could be used such as alpha blending to create a transparent image.

Combined image and NTV pixel data are then processed in a back end processor 250 that performs such video processing functions as JPEG compression before being displayed on a video monitor/display 111, stored on a computer readable medium or transmitted to a remote location viewing or storage.

Figure 2D:
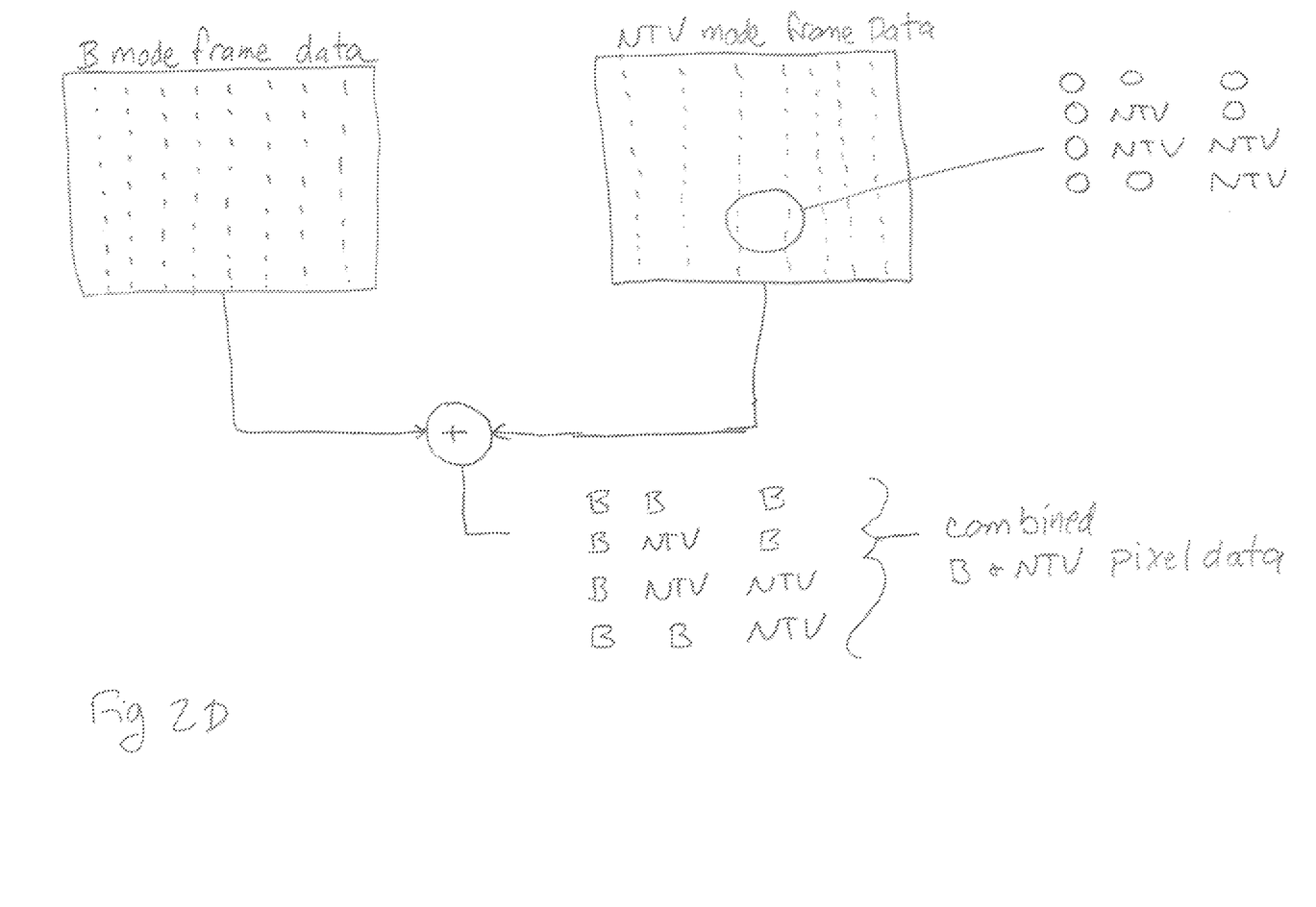
FIG. 2D illustrates how B-mode and needle tip visualization (NTV) data are combined to create an image in accordance with an embodiment of the disclosed technology.

FIG. 2D shows one possible implementation of a tissue/NTV data decision in accordance with an embodiment of the disclosed technology. In one embodiment, echo data in a photoacoustic frame tested to determine if the echo intensity is above a threshold that defines a needle tip. If so, the data is marked as NTV data, otherwise the echo data is marked as having a zero intensity. B-mode image data and NTV image data are then combined by replacing B-mode data in a combined image with NTV data. As will be appreciated, other more sophisticated methods of decision and blending the B-mode and photoacoustic data could also be performed such as by alpha-blending or the like.

As described above, in some embodiments of the disclosed technology, the ultrasound imaging machine 110 is configured to support line-triggered laser firing and to use conventional beamforming paths to form photoacoustic image lines for each frame. In some embodiments, the ultrasound machine 110 can be configured to send out a trigger signal for each photoacoustic line to be acquired alternately with the B-mode firings. In other embodiments, the ultrasound system acquires a B-mode image frame and then acquires a NTV image frame using one or more laser firings.

There can be advantages to using a line-based method versus a frame-based method depending on the system architecture. One advantage of the line-triggered method is that it utilizes an existing system design and signal processing chains. No hardware changes are needed to implement photoacoustic imaging even for older ultrasound systems or portable systems that lack CPU/GPU/FPGA processing power or a large memory to store radio frequency element data or a fast bus to transfer the data to different parts of the computational devices. Moreover, a line-triggered photoacoustic imaging system may not require a large memory to store RF element data nor a fast CPU/GPU/ASIC/FPGA to perform software beamforming. The software-based beamforming using FFT algorithm applies only to linear transducers. For curved and phased transducers, the traditional delay-and-sum method has to be used. But this algorithm is slow to be done by software. The line-triggered method alleviates these kinds of issues. In some embodiments, for example, the disclosed technology is implemented on a conventional lower-cost and/or portable ultrasound imaging machine. In some embodiments, the line-triggered method can be performed using hardware-based receive beamforming that includes a delay-and-sum method that can be applied to different types of transducers (e.g., linear, curved and/or phased).

External Laser Light Source

FIG. 3 is functional block diagram of an external laser light source 350. In the embodiment shown, the laser light source includes three printed circuit boards: a control board 352, a laser driver board 254 and a power board 356. The power board 356 is configured to receive a supply voltage from a connected ultrasound imaging machine and provide the appropriate power levels to run the circuitry in the laser light source. The control circuit board 352 includes an FPGA or a processor with an external or built-in memory that is configured to communicate with the attached ultrasound imaging machine and to receive the trigger signals which cause the laser to fire. The laser driver board 354 is configured to receive control signals from the control board 352 and supply the appropriate driving signals to the laser source to produce laser pulses when requested. In one embodiment, the external laser light source 350 is configured to communicate with the ultrasound imaging machine using the I2C communication protocol via a cable that is connected to an EKG port on the ultrasound imaging machine. Other wired or wireless communication protocols and ports could be used.

A receptacle optical assembly 360 is configured to receive a standardized style of fiber connector having one or more optical fibers that extend to the distal tip of an interventional instrument (e.g. a needle). The receptacle assembly includes a laser source such as a laser diode 362 and an optical coupler and lens that direct light from a laser diode into the optical fibers. In addition, one embodiment of the optical assembly includes a micro-switch 366 that closes when the optical fibers are connected to the optical assembly 360. In one embodiment, the optical assembly 360 also includes a mechanical or electrical optical shutter 368 that is placed between the laser diode and the optical fibers and that is physically moved or made transparent when the optical fibers are connected. An LED printed circuit board 358 supports a number of LEDs that are illuminated depending on the operating condition of the laser light source as will be described.

Further details of the external laser light source can be found in commonly owned U.S. patent application Ser. No. 15/612,725 (titled "LASER LIGHT SOURCE FOR INSTRUMENT TIP VISUALIZATION", which is filed concurrently herewith and which is herein incorporated by reference in its entirety).

As indicated above, the laser light source 350 is configured to produce laser pulses that are transmitted via the one or more optical fibers 142 to the tip 135 of the interventional instrument 130. Upon connecting the laser light source to the ultrasound imaging machine, the control printed circuit board 352 is programmed to generate or recall a device ID from a memory and transmit it to the connected ultrasound imaging system. The device ID informs the ultrasound imaging machine that the unit is cable of producing laser pulses for needle tip visualization. Upon receipt of the device ID, the ultrasound imaging machine activates the photoacoustic imaging mode. Once a user has inserted an optical fiber into the laser light source, the control printed circuit board sends a signal to the ultrasound machine that informs it that it is ready to produce laser pulses. As indicated above, the micro-switch 366 in the optical assembly is positioned so that it changes state when the user inserts the optical fibers into the optical assembly. If the optical fibers are purposely or accidentally removed from the laser light source 350, the micro-switch 366 changes state again and a signal is sent to the connected ultrasound system to suspend or halt the photoacoustic/NTV imaging process.

In some embodiments, the micro-switch 366 can be replaced with another type of sensor (e.g., a relay, a Hall effect sensor etc.) in the optical assembly that detects proper connection of the one or more fibers 142. In certain embodiments, the software that initiates the photoacoustic imaging mode is configured to start a procedure upon detection of an optical fiber(s) to allow the system start the laser firing, without the operator having to use a sterile hand or to rely on a helper to initiate the procedure via the user interface.

Figure 4:
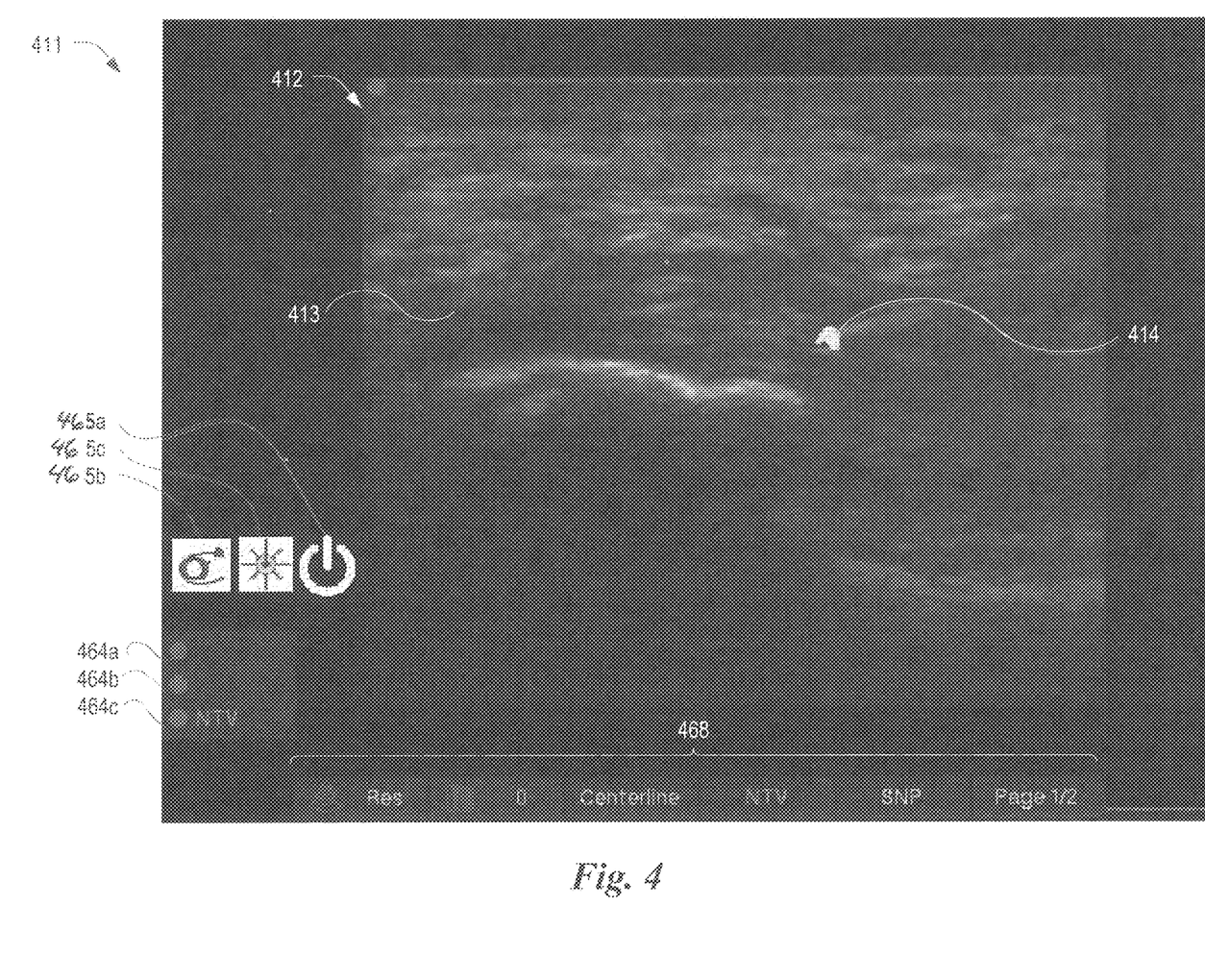
FIG. 4 is a representative screenshot of an ultrasound image with including an image of a needle tip in accordance with an embodiment of the disclosed technology.

Once the fibers are inserted into the laser light source, the control printed circuit board 352 monitors the communication connection to the ultrasound imaging machine for the trigger signals that indicate when a laser pulse should be fired. Upon receipt of a trigger signal, the control board 352 causes the laser diode to fire one or more pulses into the connected optical fibers. As discussed above with reference to FIGS. 1A-1C and 2, the laser signals are absorbed by the light absorbing medium 148, which generates corresponding photoacoustic signals that are detected by the ultrasound imaging machine 110. The ultrasound imaging machine 110 uses the detected photoacoustic signals to form an ultrasound image of the tip 135 of the interventional instrument relative to surrounding tissue FIG. 4 is a screenshot of an exemplary user interface 411 produced by the ultrasound imaging machine 110 (FIGS. 1A and 1C). The user interface 411 includes an ultrasound image 412 showing both tissue 413 in the region of interest and a colorized tip of the interventional instrument 414 (e.g., the tip 135 of FIGS. 1A-1C). A plurality of user input controls 468 can be configured to receive touch inputs from an operator to control various functions of the ultrasound imaging machine 110. Indicators 465 (identified individually as a first indicator 465a, a second indicator 465b and a third indicator 465c) provide visual cues that the laser light source is connected and powered (465a), has an optical fiber connected (465c) and that the laser is firing (465c). In some embodiments, the ultrasound system 110 can be configured to provide one or more tactile, light, color change of the graphic 414 or/and audio feedback could confirm proper operation. In some embodiments, the color of the user interface on the ultrasound imaging machine provides cues about the NTV accessory connected. For example, text in gray shows that the laser light source is connected and is executing the proper software version and the applicable transducer is present and the proper exam type has been selected. White lettering on the user interface indicates that the needle is present but the laser is not firing or the system is in freeze mode. Yellow lettering on the user interface indicates that the laser is firing. These color text indicators could be saved together with the image for record.

In some embodiments, the ultrasound imaging machine 110 provides gain control for the colorized tip ultrasound image to provide the user a means to trade off sensitivity with noise. For example, for a deeper target, the user might want to use higher gain to boost the sensitivity but tolerate more noise and artifacts. In one embodiment, the third indicator 464c is an indicator for the NTV gain control while 464a and 464b are for normal tissue and overall gain control.

Figure 5:
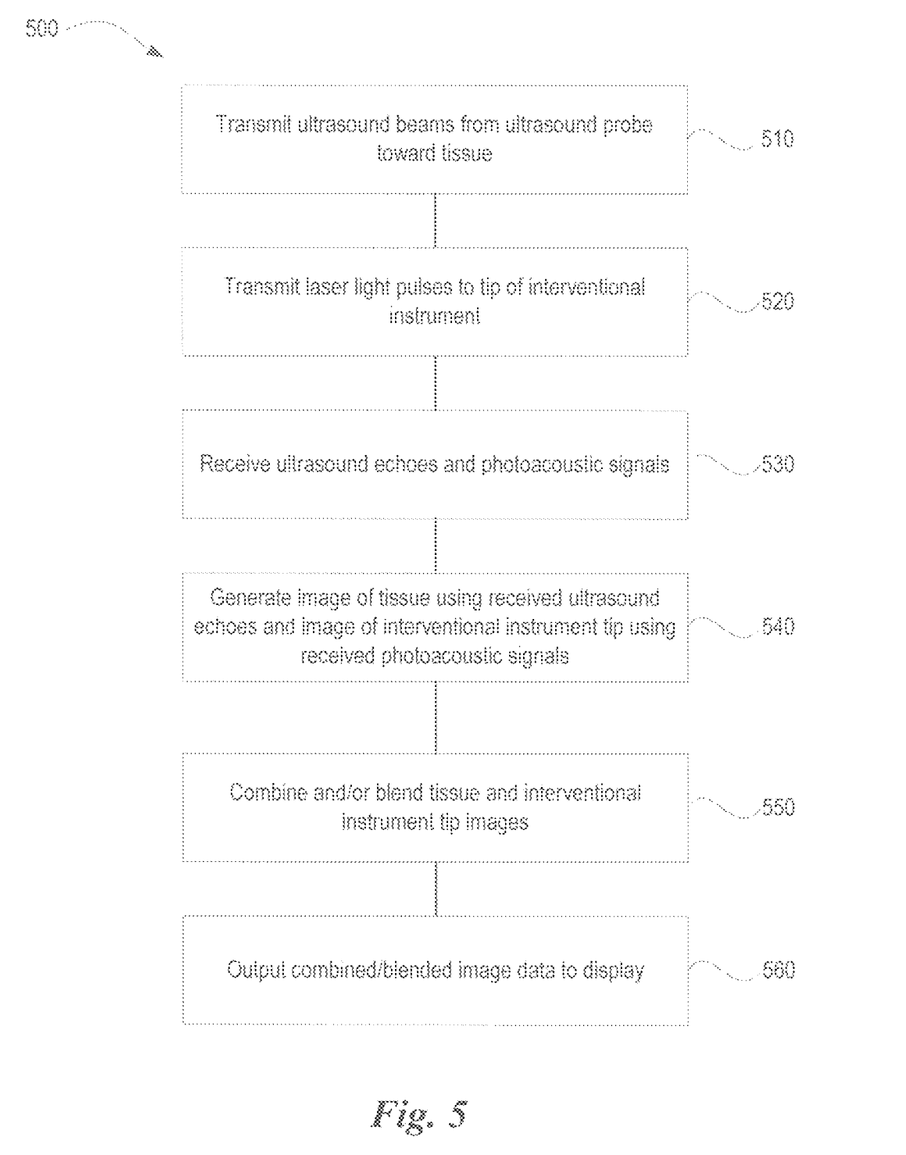
FIG. 5 is a flow diagram of a process of forming an ultrasound image in accordance with an embodiment of the disclosed technology.

FIG. 5 is an exemplary flow diagram of a process 500 of forming an ultrasound image having a colorized tip ultrasound image indicative of a tip of an interventional instrument (e.g., the tip 135 of the interventional instrument 130). In some embodiments, the process 500 is implemented with instructions stored in memory (e.g., memory 121 of FIG. 1C) and configured to be executed by a processor (e.g., the processor 117 of FIG. 1C) of an ultrasound imaging system (e.g., the ultrasound system of FIGS. 1A and 1C). In other embodiments, the process 500 can comprises instructions stored in hardware and/or software on a suitable device or computer (e.g., a medical imaging device) or configuration of an FPGA.

At step 510, the process 500 transmits a number N (e.g., 128, 256, 512) of ultrasound beams (e.g., the pulses 118 of FIG. 1C) from an ultrasound transducer (e.g., the transducer 120 of FIGS. 1A and 1C) toward a region of interest in a subject.

At step 520, the process 500 transmits a predetermined number of corresponding laser light pulses from an external laser light source (e.g., the external laser light source 140 of FIG. 1A). As described above in reference to FIGS. 1A-1C, individual laser light pulses can be transmitted via one or more optical fibers that terminate at the light absorbing medium (e.g., a black epoxy) at a tip of an interventional instrument. The light absorbing medium absorbs the laser light pulses and generates a corresponding photoacoustic signal surrounding the tip of the interventional instrument. In some embodiments, the process 500 operates in a line-based imaging mode and transmits a laser light pulse that is interleaved with each of the number N (e.g., 32 to 512 is a typical range of number of lines per frame) of ultrasound beams transmitted at step 510. In other embodiments, the process 500 operates in a frame-based imaging mode and transmits a number of laser light pulses that are not interleaved with the number N ultrasound beams at step 510. In photoacoustic mode imaging, the transmitter is shut down and there is minimum or no ultrasound energy output from the transducer. The entire photoacoustic image frame could be interleaved with normal tissue imaging frame: B+PA+B+PA . . . , therefore, the transmitter is shut down every other frame. In certain embodiments, however, a block of photoacoustic lines could be interleaved with a block of normal tissue imaging lines. In some embodiments, the process 500 operates in a subframe-based imaging mode and transmits one or more laser light pulses (e.g., 4, 8, 16, 32) and then transmits and receives of a number of N ultrasound beams at step 510 for normal tissue imaging.

At step 530, the process 500 acquires ultrasound data corresponding to ultrasound echoes (e.g. detected ultrasound echoes 119 of FIG. 1C) received from the region of interest. The process further acquires photoacoustic data corresponding to the photoacoustic signals generated from the tip of the interventional instrument at step 520.

At step 540, the process 500 constructs a combined image using the acquired ultrasound echoes and the photoacoustic data acquired at step 530. A photoacoustic/B-mode decision has to be made to each pixel before combining them. A simple threshold or a complex fuzzy logic algorithm could be used.

At step 550, the process 500 combines and/or blends the data from the two imaging modes at step 540 to form a combined image.

At step 560, the process 500 outputs the combined image to a display (e.g., the display 111 of FIG. 1C) as shown, for example, in FIG. 4. The combined image includes image data corresponding to background tissue in the region of interest and colorized image data corresponding to the tip of the interventional instrument. In some embodiments, the background tissue is shown in gray while the image data corresponding to the tip of the interventional instrument is shown in an operator-desired color (e.g., red, yellow, blue, orange). In some embodiments, yellow is the preferred color for the pixels representing the instrument tip because yellow is not generally associated with other ultrasound imaging modes and is easily seen by users—even those with red and green color impaired vision.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A system, comprising:
   a transducer configured to transmit ultrasound signals including ultrasound beams toward a region of interest in a subject and to receive additional ultrasound signals from the subject;
   an external laser light source configured to produce laser light pulses upon receipt of a trigger signal;
   one or more optical fibers having a first end and a second end, wherein the first end is configured to be optically coupled to the external laser light source and the second end includes an absorber configured to be attached to a tip of an interventional instrument and to produce photoacoustic signals at the second end in response to the laser light pulses being transmitted through the first end; and
   an ultrasound imaging machine including a processor configured to:
      combine echo data based on the additional ultrasound signals and photoacoustic data based on the photoacoustic signals to produce a combined image that shows both a tissue in the region of interest and the tip of the interventional instrument;
      generate the trigger signal when an energy of the ultrasound signals is reduced to a minimal energy;
      interleave a plurality of the laser light pulses with a plurality of the ultrasound beams, and
      transmit a control signal to the transducer to reduce the energy of the ultrasound signals to the minimal energy when the laser light pulses are generated by the external laser light source in response to the trigger signal to synchronize the laser light pulses with the ultrasound signals having the minimal energy transmitted by the transducer.

2. The system of claim 1, wherein the processor is configured to:
   reduce the energy of the ultrasound signals to the minimal energy by reducing the amplitude of the ultrasound signals.

3. The system of claim 1, wherein the processor is configured to:
   reduce the energy of the ultrasound signals to the minimal energy by reducing a duration of the ultrasound signals.

4. The system of claim 1, wherein the processor is configured to:
   receive a signal from the external laser light source indicating that an optical fiber has been inserted into the external laser light source and to begin operating in a needle tip visualization mode.

5. The system of claim 1, wherein the processor is configured to:
   interleave each of the plurality of the laser light pulses with each of the plurality of the ultrasound beams; and
   receive the additional ultrasound signals interleaved with the photoacoustic signals.

6. The system of claim 1, wherein the processor is further configured to:
   colorize photoacoustic and B-mode pixel data separately prior to displaying the combined image of the tip of the interventional instrument in the region of interest.

7. The system of claim 1, wherein the interventional instrument is a needle and the second end is positioned adjacent a tip of the needle.

8. The system of claim 1, wherein the processor is configured to generate a trigger delay to compensate for a time delay between a first time at which the trigger signal is transmitted to the external laser light source and a second time at which a laser pulse is generated by the external laser light source in response to the trigger signal to align a photoacoustic image frame associated with the photoacoustic data with an ultrasound image frame associated with the echo data.

9. The system of claim 1, wherein the processor is configured to determine that an intensity of the photoacoustic data is greater than a predetermined threshold to mark the photoacoustic data as being associated with the interventional instrument.

10. An ultrasound imaging machine, comprising:
   a transducer configured to transmit ultrasound signals including ultrasound beams toward a region of interest in a subject and to receive additional ultrasound signals from the subject;
   a processor configured to:
      combine echo data based on the additional ultrasound signals and photoacoustic data based on photoacoustic signals produced by laser pulses from an external laser light source to create a combined image that shows a tissue in the region of interest and a tip of an interventional instrument;
      generate a trigger signal to the external laser light source to generate the laser pulses;
      generate a control signal to the transducer to reduce an energy of the ultrasound signals transmitted by the transducer to a minimal energy to synchronize the laser pulses with the ultrasound signals having the minimal energy transmitted by the transducer, wherein the laser pulses are transmitted through a first end of one or more optical fibers that is coupled to the external laser light source to a second end of the one or more optical fibers comprising an absorber that is coupled to a tip of the interventional instrument for the absorber to produce the photoacoustic signals in response to the laser pulses.

11. The ultrasound imaging machine of claim 10, wherein the processor is configured to:
reduce the energy of the ultrasound signals to the threshold minimal energy by reducing an amplitude of the ultrasound signals in response to the control signal.

12. The ultrasound imaging machine of claim 10, wherein the processor is configured to:
reduce the energy of the ultrasound signals to the t energy by reducing a duration of the ultrasound signals in response to the control signal.

13. The ultrasound imaging machine of claim 10, wherein the processor is configured to:
begin operating in an instrument visualization mode upon receipt of a signal from the external laser light source that indicates that the one or more optical fibers have been connected to the external laser light source.

14. The ultrasound imaging machine of claim 10, wherein the processor is configured to:
stop operating in an instrument visualization mode upon receipt of a signal from the external laser light source that indicates that the one or more optical fibers have been disconnected from the external laser light source.

15. The ultrasound imaging machine of claim 10, wherein the processor is further configured to interleave each of the laser pulses with each of the ultrasound beams.

16. A method of operating an ultrasound imaging machine to form an ultrasound image of a region of interest including a colorized ultrasound image showing a tissue and a distal tip of an interventional instrument in the region of interest, the method comprising:
transmitting ultrasound signals including ultrasound beams toward the region of interest from an ultrasound transducer;
acquiring ultrasound echo data based on additional ultrasound signals that are received in response to the ultrasound signals transmitted;
generating a trigger signal to an external laser light source to produce laser pulses, wherein the laser pulses are transmitted through a first end of one or more optical fibers that is coupled to the external laser light source to a second end of the one or more optical fibers comprising an absorber that is coupled to the distal tip of the interventional instrument for the absorber to produce photoacoustic signals in response to the laser pulses;
generating a control signal to the ultrasound transducer to reduce an energy of the ultrasound signals transmitted by the ultrasound transducer to a minimal energy to synchronize the laser pulses with the ultrasound signals having the minimal energy transmitted by the ultrasound transducer;
acquiring photoacoustic echo data from the photoacoustic signals; and
combining the ultrasound echo data and the photoacoustic data to produce a combined image that shows the tissue in the region of interest and the distal tip of the interventional instrument.

17. The method of claim 16, further comprising:
interleaving each of the laser pulses with each of the ultrasound beams.

18. The method of claim 17, further comprising:
detecting a signal from the external laser light source that indicates a connection of the one or more optical fibers to the external laser light source; and
automatically entering an instrument visualization mode in response to detecting the signal.

19. The method of claim 18, further comprising:
detecting a signal from the external laser light source indicating that the one or more optical fibers have been removed from the external laser light source; and
automatically ceasing transmission of the trigger signal upon receipt of the signal indicating the removal of the one or more optical fibers from the external laser light source.

20. The method of claim 16, wherein the interventional instrument includes a needle.

* * * * *